United States Patent
Calderini et al.

(10) Patent No.: US 7,183,315 B2
(45) Date of Patent: Feb. 27, 2007

(54) SILVER SALTS OF SUCROSE-OCTASULPHATE

(75) Inventors: Gabriella Calderini, Due Carrare (IT); Marco Prosdocimi, Padova (IT); Claudio Antico, Cerro Maggiore (IT); Giuliana Miglierini, Varese (IT); Danilo Casadei Massari, Padova (IT)

(73) Assignee: Interalia S.R.L., Padova (IT)

( * ) Notice: Subject to any disclaimer, the term of this patent is extended or adjusted under 35 U.S.C. 154(b) by 418 days.

(21) Appl. No.: 10/492,342

(22) PCT Filed: Oct. 17, 2002

(86) PCT No.: PCT/EP02/11627

§ 371 (c)(1), (2), (4) Date: Apr. 9, 2004

(87) PCT Pub. No.: WO03/035656

PCT Pub. Date: May 1, 2003

(65) Prior Publication Data

US 2004/0254366 A1    Dec. 16, 2004

(30) Foreign Application Priority Data

Oct. 19, 2001    (IT) ........................ MI2001A2188

(51) Int. Cl.
 *A61K 7/48* (2006.01)
 *A61K 31/70* (2006.01)
(52) U.S. Cl. .................. 514/460; 549/210; 556/111
(58) Field of Classification Search ............... 514/460; 549/210; 556/111
See application file for complete search history.

(56) References Cited

U.S. PATENT DOCUMENTS 4,357,326 A    11/1982    Nair et al. ............... 424/180

FOREIGN PATENT DOCUMENTS

| EP | 023023 A2 | 7/1987 |
|---|---|---|
| EP | 0348143 A2 | 12/1989 |
| WO | WO 98/22114 | 5/1998 |
| WO | WO 98/31697 | 7/1998 |

OTHER PUBLICATIONS

Schierholz et al., "*Efficiency of Silver-Coated Medical Devices*", Institute of Medical Microbiology and Hygiene, University of Cologne 1998, pp. 257-262.
Scalzo et al.,"*Utilization of Electrochemical Silver Ions As Preservative Agent In Cosmetic Dispersions*", International Journal of Cosmetic Science, 19, pp. 27-35, 1997.
Paimela et al., "*Restitution of Frog Gastric Mucosa In Vitro: Effect of Basic Fibroblast Growth Factor*", The American Gastroenterological Association, vol. 104, No. 5, 1993, pp. 1337-1345.
Folkman et al., "*Duodenal Ulcer, Discovery of a New Mechanism and Development of Angiogenic Therapy That Accelerates Healing*", Presented at the 11th Annual Meeting of the American Surgical Association, Apr. 11-13, 1991 pp. 414-427.
"*Disinfection Sterilization and Preservation*", 4th Edition, SS Block Ed., Lea & Febiger Chicago, 1990, pp. 718, 720-722, 824.
Gilman et al. "*The Pharmacological Basis of Therapeutics*", 4th Edition, Maxwell Macmillan Int. Eds., New York, 1970 pp. 1049-1050.

*Primary Examiner*—Taofiq Solola
(74) *Attorney, Agent, or Firm*—Ohlandt, Greeley, Ruggiero & Perle, L.L.P.

(57) ABSTRACT

The described invention relates to the new compound "sucrose-octasulphate salified with silver" usefully applicable in the prevention and cure of infections by microorganisms of bacterial, fungal, viral and/or yeast origins and in the promotion of tissue repair. The silver salts of sucrose octasulphate, subject of the invention have in fact been shown to possess antimicrobial activities even higher than that of known silver compounds. These properties therefore make them particularly suitable for use in different pathological or paraphysiological conditions of the skin, of the epithelia and of the mucosa both intact and lesioned.

13 Claims, No Drawings

SILVER SALTS OF SUCROSE-OCTASULPHATE

FIELD OF THE INVENTION

The present invention relates to the new compound "sucrose-octasulphate salified with silver" for use in compositions usefully applicable in pathological or paraphysiological conditions of the skin, of the epithelia and of the mucosa in the prevention and treatment of infections sustained by different types of microorganisms and in the promotion of tissue repair.

STATE OF THE ART

It is widely known that in pathologies characterised by lesions of the epidermal and dermal layers, such as for example ulcers and burns, treatments are essentially devoted to promote/accelerate the processes of tissue repair in aseptic conditions. In fact, infections constitute one of the major problems in the treatment of cutaneous lesions and the onset of infections resistant to antibiotics represents a serious problem in the clinical management of these pathologies further, complicated by the limited choice of antibiotic agents available for this purpose. For example, infections constitute one of the most serious complications of burns, even of small dimensions; in the most serious cases they represent the primary cause of death and in addition are involved in the appearance of disfiguring scaring or disabling outcomes.

For the treatment of these pathologies it is therefore necessary to address the attention towards therapeutic agents capable, on the one hand, of promoting tissue repair as well as supporting or increasing the physiological processes of tissue repair, and on the other, of opposing, from the beginning and until scar formation has occurred, the colonisation of cutaneous tissues by pathogenic agents.

For a long time silver has been recognised as a useful therapeutic agent in the prevention of infections. Silver nitrate at a concentration of 10% has in fact been used in clinical practice for the treatment of cutaneous lesions since the last century, though later abandoned due to its toxicity. Currently, silver nitrate at 0.5% or silver sulphadiazine at 1% constitute the most common and chosen treatments for burns, being capable of controlling Gram-negative infections, not effectively controlled by conventional antibiotics. Also other silver based ionisable compounds are used clinically, amongst these for example silver lactate or picrate. Also available are colloidal forms of silver, the antimicrobial activity of which depends not only on the total silver content, but on the content of free silver ions. The use of silver for the treatment of cutaneous lesions is however limited due to its toxicity, which could also be a cause of delay in tissue repair, as a consequence of its cytotoxic effect on granulation tissue.

This effect is indeed in general shared by all disinfecting agents. In addition to this cytotoxic activity, other limitations regarding the use of silver as an antimicrobial agent exist: i) the precipitation of silver chloride upon contact of the silver with biological fluids, with consequent reduction of its antimicrobial strength, ii) its possible binding to serum albumin which, in addition to a loss in effectiveness, gives rise also to the possibility of later systemic absorption of the same silver and iii) its photoinstability and the staining of the tissues with which it comes into contact (J. M. Schierholz, L. J. Lucas, A. Rump, G. Pulverer, *J. Hospital Infection*, 40, 257–262, 1998; in "The pharmacological basis of therapeutics", A. Goodman Gilman, T. W. Rall, A. S. Nies, P. Taylor Eds. $4^{th}$ Ed., *Maxwell Macmillan Int. Eds.*, New York, pp. 1049–1050, 1970).

The use and efficacy of silver derivatives against pathogenous agents of various types, for example bacteria, moulds, yeasts and viruses are also known; for this activity silver has been used as a preservative in cosmetic preparations, showing activity against *Pseudomonas aeruginosa, Candida albicans* and *Staphylococcus aureus* at concentrations of $10^{-5}$ M silver (M. Scalzo, F. Cerretou, C. Orlandi, N. Simonetti, *Int. J. Cosmetic Sci.*, 19, 27–35, 1997).

Sucrose-octasulphate (SOS) is a compound, already known and used, for example in the form of an aluminium salt in sulcralfate, a compound widely used in the therapy of gastro-intestinal ulcers. The protective effect of sulcralfate seems to be linked in part to the buffering effect performed by aluminium hydroxide, as well as the ability of sucrose-octasulphate to protect the gastric epithelium, an effect which probably arises from its ability to form a protective barrier on the area of the lesion. Sulcralfate is in fact an insoluble compound which, in acidic environment, can polymerise forming a viscous substance capable of adhering to the gastric epithelium.

Data from the literature lead one to hypothesise that sucrose octasulphate can favour the bioavailability of trophic factors locally released. These would be capable of favouring the re-epithelialisation of the lesioned area. This mechanism, described for the gastric epithelium, could have a functional effect also at the cutaneous level (J. Folkman, S. Szabo, M. Strovoff, P. McNeill, W. Li, Y Shing, *Ann. Surg.*, 214, 414–427, 1991; H. Paimela, P. J. Goddard, K. Carter, R. Khakee, P. L. McNeill, S. Ito, W. Silen, *Gastroenter.*, 104, 1337–1345, 1993).

SUMMARY OF THE INVENTION

Now the applicant has surprisingly found that silver salts of sucrose-octasulphate (SOS-Ag) can be advantageously used for prevention and therapy of infections sustained by microorganisms of different types (bacterial, fungi, virusesal and/or yeasts) and for the promotion/acceleration of tissue repair in pathologies of skin, of mucosa and of epithelia both intact and lesioned, characterised by potential or actual infections sustained by pathogens of various types, such as for example fungal infections or ulcers.

The subject of the present invention is therefore the compound of formula (I)

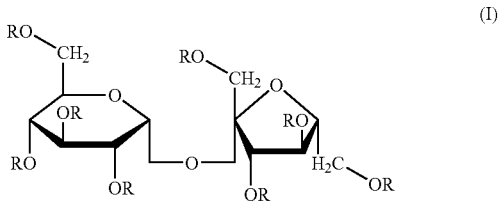

wherein R is $SO_3^- Ag^+$

A further subject of the invention relates to the synthetic processes characterised by: a) preparation of sucrose-octasulphate in acid form (SOS-H) and its successive salification either by neutralisation in solution with Ag ion bases up to pH 7.2, or by passing through a column of ion exchange resin derivatised with Ag ions; b) direct exchange between sucrose-octasulphate salts and silver salts. Still another subject of the invention is the use of the compounds for treatment in the prevention and/or therapy of bacterial, fungal, viral and/or yeast infections and in the promotion/acceleration of tissue repair in pathologies of skin, mucosa and of epithelia, both intact and characterised by lesions of the epidermal and/or dermal layers.

DETAILED DESCRIPTION OF THE INVENTION

The aims and the advantages of the present invention, will be better understood throughout the course of the following invention in detail.

The compound SOS-Ag of formula (I)

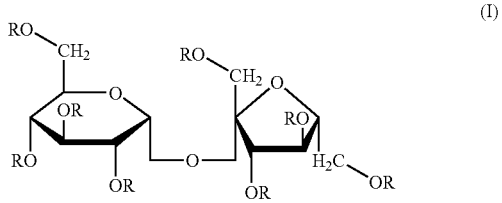

(I)

wherein R is $SO_3^-$ $Ag^+$ can be obtained according to known methods which usually involve the direct exchange of sodium salts of SOS, or salts of other alkaline metals, with other counterions of interest. These processes have however the disadvantage of not corresponding to a stoichiometric exchange, with a significant effect on the yields and the Ag titre of the final product. A further limitation connected with this method is the achievement of unstable products, as a consequence of the high acidity due to the possible formation of sulphuric acid.

The first synthetic process devised with the aim of overcoming the above mentioned problems is characterised by two distinct steps which consist of: a) preparation of SOS-H starting from a salt of SOS with for example monovalent cations such as Na and K; b) neutralisation, under controlled conditions up to pH 7.2, of the SOS-H with Ag ion bases (for example oxides, hydroxides, bicarbonates and carbonates).

The second synthetic process is characterised by: a) preparation of SOS-H starting from a salt of SOS with for example monovalent cations such as Na and K; b) preparation of resins derivatised with Ag ions through activation with strong bases and later exchange with salts or oxides of Ag and c) passing the acid form product obtained in step a) through the columns obtained in step b).

The third synthetic process is instead characterised by the direct exchange between sodium or potassium salts of sucrose-octasulphate with Ag salts selected for example from $AgBF_4$, $AgClO_4$, $AgNO_3$ and $Ag_2CO_3$. The exchange reaction between monovalent salts of SOS and $AgBF_4$ results as being the preferred, in that it gives a final product with a high Ag titre and has a good yield.

The exchange reaction must however be carried out in suitable conditions to overcome the above mentioned problems; in particular it appears to be essential that the exchange reaction be carried out in the dark, in an aqueous environment and in the absence of solvents, as well as it is also essential to eliminate the tetrafluoroborate salt obtained as a product of the exchange reaction with the starting sucrose-octasulphate monovalent ion.

Herein, examples of the preparation of SOS-Ag are described, with the purpose of non-limiting illustration of the present invention, being a person skilled in the field able to introduce all the modifications and the improvements suggested through normal experience and by the natural evolution of the technique, without departing from the scope of the present invention.

EXAMPLE 1

Method of Synthesis of SOS-Ag

Commercial SOS-K has been purified with the aim of reducing the amounts of impurities present and in particular the chloride and sulphate content, obtaining SOS-K containing less than 0.1% chloride and sulphate. 10 g of SOS-K have been therefore solubilised in 150 ml of double distilled water. The solution thus obtained has been percolated through Amberlite IR 120 H ion exchange resin, collecting the acidic eluate fractions. The resin has then been washed twice with 35 ml of double distilled water. The acidic solution (pH 1.5) collected after ion exchange resin passage has been stored in an ice bath to avoid possible desulphatisatoin of the product. All of the subsequent operations have been carried out by working in the absence of light, natural or artificial, and can also be conveniently carried out in a dark room.

The SOS-H solution has then been subjected to stirring, under continuous monitoring of the pH with a pH meter. 6.4 g of $Ag_2O$ have been added, to reach a pH of 7.2 (theoretical $Ag_2O$=7.2 g). The solution of SOS-Ag obtained has been kept stirring for 4–5 hours and then filtered under reduced pressure through a porous septum coated with Celite HSS. Following filtration an opalescent solution has been obtained which has been again filtered through Celite until a clear solution was obtained. The final solution has been taken to dryness in a rotary evaporator in a thermostated water bath at 60–65° C. under reduced pressure. The residue, constituted by a spongy-glasslike solid, has been treated with 50 ml of acetone and again evaporated to dryness under reduced pressure. The solid residue, obtained in the form of shiny off-white flakes, has been collected and washed twice with 70 ml of acetone and, after brief stirring, has been decanted eliminating the overlying acetone. The solid has been finally purified from the residual acetone by evaporation of the latter in a rotating evaporator in a thermostated water bath at 60–65° C. under reduced pressure. All the final manipulations of the solid have been carried out in the absence of light.

Yield 13.3 g SOS-Ag (93%) Ag titre: 45.7%, equal to 97.2% of the theoretical value (47%)

Appearance: shiny, almost white flakes

Solubility: very soluble in water; particularly insoluable in organic solvents.

EXAMPLE 2

Method of Synthesis of SOS-Ag 2 g of commercial SOS-K, previously purified as reported in example 1, has been solubilised in 30 ml of double distilled water and the solution thus obtained has been percolated through Amberlite IR 120 H ion exchange resin, collecting the acidic eluate fractions. The resin has then been washed twice with 10 ml of double distilled water. The acidic solution (pH 1,5) collected after ion exchange resin passage has been stored in an ice bath. All the following operations have been carried out by working in the absence of light, natural or artificial, and can also be conveniently carried out in a dark room.

A solution of 7.8 g of Silver nitrate in 100 ml of double distilled water has been eluted through a second column of Amberlite IRC 50 resin previously activated with a solution of 0.5 N KOH. By this procedure one obtains a column of resin derivatised with Ag ions. Following a wash with water, the acid form SOS-H obtained previously has been eluted through the second column, derivatised with Ag ions, obtaining an eluate constituted by SOS-Ag. The eluate has been collected and, while kept in the dark, taken to dryness. The resulting solid has been washed twice with acetone and then decanted. The compound obtained, constituted by a white solid, has been subsequently dissolved in double distilled water and re-crystallised.

Yield 2.2 g SOS-Ag (77%);

The characteristics of the product correspond with these reported in example 1.

EXAMPLE 3

Method of Synthesis of SOS-Ag

KSOS (7.13 g corresponding to 1 eq) is dissolved in 5 volumes of distilled $H_2O$ (35.6 ml) at T=40° C. in a dark, screw-topped beaker. The solution is left to cool to room temperature.

Solid $AgBF_4$ (8.37 g=0.97 eq) is added, whilst working in a dark room. Immediately, a suspension of a fine precipitate is formed. It is left stirring for 2 hours and the $KBF_4$ precipitate (4 g) is filtered using a Buchner funnel fitted with a paper filter (Whatman filter papers 5; 55 mm Ø).

The clear solution is then filtered through a nylon membrane with a porosity of 0.45 μm (Superchrom syringe filters 25 mm Ø).

The clear filtrate is collected (43 ml) and the water is completely removed by distillation at a temperature between 20° C. and 40° C.

The product is washed with acetone (20 ml). The solvent is removed and another aliquot (20 ml) is added and left stirring for 10 minutes. The white solid obtained is filtered with a Pyrex glass filter funnel (cylindrical with a porous septum of porosity 3) and it is washed on the filter with a further aliquot of acetone (30 ml), paying attention not to allow the product to dry for an overlong time. Being highly hygroscopic it tends in fact to become adhesive.

The solid obtained is transferred to vials and dried at room temperature in a crystalliser under vacuum.

Yield: 9.84 g (93%); Ag titre: 93%;

Appearance: white cyrstalline, fine powder.

The results obtained from the synthesis and the stability data indicate that, unexpectedly, from the salification reaction between SOS-H and Ag bases one obtains compounds which are stable in aqueous solution at neutral or slightly acidic pH, whilst it is known that Ag salts are stable in solution only in very acidic environments. Also, the SOS-Ag obtained according to example 3 results as having good stability, both in the solid state and in aqueous solution, whilst it is a particular industrial advantage, having a single step method.

The methods of synthesis herein outlined, besides the attainment of a stable product, present also other advantages with regard to industrial applicability, in particular for the high yield of product and for the high Ag titre.

Antimicrobial Activity of SOS-Ag

The antimicrobial activity of the compound, subject of the present invention, SOS-Ag, having a Ag titre of 42.51%, has been verified by comparison of the same with equimolar concentrations of the commercial product Katoxyn powder, having a Ag titre of 4.25%.

The antimicrobial activity has been evaluated according to the experimental design described below.

1. Bacterial Growth Inhibition Test in Culture Broth

Serial dilutions of known titre of the two products SOS-Ag and Katoxyn, the latter containing Ag in the form of metallic silver (silver Katadyn® collodial chemical), have been placed directly in contact with the test microorganism (*Staphylococcus Aureus* ATCC 6538) for incubation in culture broth under agitation. The effect of the substances on cellular growth has been measured by evaluating the absence of turbidity in the culture medium. The anti bacterial activity has been verified by the seeding of 1 ml of culture broth in an agarised medium, with observations at 7, 14, 21, 28 days from the beginning of the experiment (tables 1 and 2).

2. Bacterial Growth Inhibition Test by Diffusion in Agar

The inhibition of bacterial growth has been, in this case, evaluated on a confluent bacterial culture of *Staphylococcus aureus* ATCC 6538 obtained on solid medium, according to the seeding method for inclusion. Serial dilutions of the test products, of known Ag titre, have been deposited inside 8 mm diameter wells formed in the medium in direct contact with the bacteria *Staphylococcus aureus* ATCC 6538. The antibacterial activity of the products under test have been evaluated, after appropriate incubations, by measuring the halos of inhibition around each well (tables 3 and 4).

The results obtained are reported in the following tables, summarised according to the different experimental methods used:

TABLE 1 inhibition of *S. aureus* ATCC 6538 growth by SOS-Ag: growth method in culture broth

| Ag titre | Incubation times | | | |
|---|---|---|---|---|
| | 7 days | 14 days | 21 days | 28 days |
| $1 \times 10^{-2}$ M | + | + | + | + |
| $1 \times 10^{-3}$ M | + | + | + | + |
| $5 \times 10^{-4}$ M | − | − | − | − |
| $1 \times 10^{-4}$ M | − | − | − | − |
| $1 \times 10^{-5}$ M | − | − | − | − |
| Positive control: ampicillin | + | + | + | + |

(− growth; + inhibition)

TABLE 2 inhibition of *S. aureus* ATCC 6538 product Katoxyn: growth method in culture broth

| Ag titre | Incubation times | | | |
|---|---|---|---|---|
| | 7 days | 14 days | 21 days | 28 days |
| $1 \times 10^{-1}$ M | + | + | + | + |
| $1 \times 10^{-2}$ M | + | + | + | + |
| $5 \times 10^{-3}$ M | − | − | − | − |
| $1 \times 10^{-3}$ M | − | − | − | − |
| $1 \times 10^{-4}$ M | − | − | − | − |
| Positive control: ampicillin | + | + | + | + |

(− growth; + inhibition)

TABLE 3 inhibition of *S. aureus* ATCC 6538 growth by
SOS-Ag: method of diffusion in agar (seeded by inclusion)

| SOS-Ag | Ag titre | | |
|---|---|---|---|
| | $1 \times 10^{-3}$ M | $5 \times 10^{-4}$ M | $1 \times 10^{-4}$ M |
| Halo of inhibition (mm) | 13 | 0 | 0 |

| Positive control: | Concentration (I.U./ml) | | |
|---|---|---|---|
| ampicillin | 20 | 10 | 5 |
| Halo of inhibition (mm) | 39 | 20 | 11 |

I.U. = international units

TABLE 4 inhibition of *S. aureus* ATCC 6538 growth by
the product Katoxyn: method of diffusion in agar (seeded by inclusion)

| Katoxyn | Ag titre | | |
|---|---|---|---|
| | $1 \times 10^{-2}$ M | $5 \times 10^{-3}$ M | $1 \times 10^{-3}$ M |
| Halo of inhibition (mm) | 12 | 0 | 0 |

| Positive control: | Concentration (I.U./ml) | | |
|---|---|---|---|
| ampicillin | 20 | 10 | 5 |
| Halo of inhibition (mm) | 39 | 20 | 11 |

I.U. = international units

From the experimental results shown above one can conclude that the product SOS-Ag is more active than Katoxyn since in the experimental conditions used has been effective at a concentration of Ag of $1 \times 10^{-3}$ M, whilst Katoxyn in the same experimental conditions has been demonstrated to be active at a concentration of Ag of $1 \times 10^{-2}$ M.

On the basis of the results shown above, the product SOS-Ag, characterised by a Ag titre of 44.7%, has been further tested in comparison with the known antimicrobial agent silver sulphadiazine, using concentrations of the two compounds equimolar in Ag.

We report below the results obtained in the evaluation of the effect of inhibition of growth of *S. aureus* ATCC 6538 through the action of the two products under test. The characterisation of the antibacterial activity has been carried out using the method of diffusion in agar, placing the substances in contact with confluent bacterial cultures on solid medium. The experiments have been carried out according to two distinct methods: 1) wetting sterile cellulose disks, 13 mm in diameter with 100 μl of solutions at serial dilutions of the product of known Ag titre. The disks have been placed in direct contact with the seeded solid medium and the appearance of halos of inhibition around the same disks after 72 hours of incubation at a 37° C. was observed and compared with a control disk containing just the solvent used to dissolve the products. The results obtained are reported in table 5. These results have been confirmed also by diffusion tests in agar according to the method of seeding by inclusion, in which on the medium supporting the confluent culture of the microorganism have been created wells having diameters of 8 mm using a sterile biopsy punch. 100 μl of the solutions containing the products at known concentrations of Ag are placed on the base of the wells, and the bacteriocidal activity is observed after 72 hours of incubation at 37° C. against a blank constituted of just the solvent used for the solubilisation of the products. (table 6).

TABLE 5 inhibition of *S. aureus* ATCC 6538 growth in
presence of SOS-Ag or silver sulphadiazine: diffusion method
in agar (disks of 13 mm)

| Compound | Ag titre (M) | Halo of inhibition (mm) |
|---|---|---|
| SOS-Ag | $10^{-2}$ | 15.3 |
| | $10^{-3}$ | 12 |
| | $10^{-4}$ | 0 |
| | $10^{-5}$ | 0 |
| Silver sulphadiazine | $10^{-2}$ | 14 |
| | $10^{-3}$ | 11.4 |
| | $10^{-4}$ | 0 |
| | $10^{-5}$ | 0 |
| Negative control | — | 0 |

TABLE 6 inhibition of *S. aureus* ATCC 6538 growth in
presence of SOS-Ag or silver sulphadiazine: diffusion method
in agar (seeded by inclusion)

| Compound | Ag titre (M) | Halo of inhibition (mm) |
|---|---|---|
| SOS-Ag | $10^{-2}$ | 14.5 |
| | $10^{-3}$ | 14 |
| | $10^{-4}$ | 0 |
| | $10^{-5}$ | 0 |
| Silver sulphadiazine | $10^{-2}$ | 14 |
| | $10^{-3}$ | 13.0 |
| | $10^{-4}$ | 0 |
| | $10^{-5}$ | 0 |
| Negative control | — | 0 |

The results obtained, reported for exemplification, but not exhaustively, on the antimicrobial properties of the compound subject of the invention, demonstrate that at parity in Ag titre, the same has activity equal to or greater than the known silver compounds normally used in therapy.

The compound SOS-Ag can therefore have the antimicrobial activity typical of the silver salts, and in particular against a number of bacterial strains (both Gram positive and Gram negative), against fungi, viruses and yeasts. We cite for example the bacteria: *Staphylococcus* sp., *Enterobacter* sp., *Clostridium* sp., *Acinetobacter* sp., *Yersinia* sp., *Pasturella* sp., *Pseudomonas aeruginosa*, *Klebsiella pneumoniae*, *Bacillus subtilis*, *Escherichia coli*, *Streptococcus* sp., *Micrococcus luteus*, *Chlamydia* sp., *Mycobacterium* sp.; the yeasts *Candida albicans*, *Candida tropicalis* and *Saccharomyces cerevisiae*; the fungi *Trichophyton rubrum*, *Aspergillus* sp., *Borrelia* sp.; the viruses: Herpes simplex virus, and Human papilloma virus. The above cited microorganisms are intended for exemplification, but not exhaustively, of the range of microorganisms on which the product SOS-Ag can exercise its antimicrobial action, being known that silver is active on many different pathogenic microorganisms, amongst which many strains resistant to normal antibiotics (*Disinfection Sterilisation and Preservation*, 4th Ed., SS Block Ed., Lea & Febiger, Philadelphia, p. 718–722, 824, 1990). Other examples and characteristics of the invention appear for this reason obvious to the expert in the art; the examples reported herein are not intended therefore to define the limits or the aims of the applicability of the product SOS-Ag. The Ag salts of sucrose-octasulphate subject of the invention possess therefore, with respect to known products, a series of advantages from the point of view of therapeutic application, inherent essentially in their stability in solutions of neutral or slightly acidic pH and their high ionic content. This confers to these Ag salts a prolonged antimicrobial action, whilst it is known that the brief duration of the therapeutic effect of the Ag salts available is one of the major restraints to the clinical use of these compounds. It is further known that the antimicrobial activity of silver depends not so much on the total quantity of metal present, but on the quantity of free ions.

The stabilisation of the Ag ions through the formation of salts with sucrose derivatives determines an improvement in the therapeutic coefficient, because it can, through a slow and more gradual release of the Ag ions, bring about a more prolonged efficacy without the appearance of the cytolesive effects that inhibit the formation of granulation tissue and slowing down of the processes of tissue repair. Furthermore the effects on tissue repair can be further potentiated by sucrose-octasulphae, of which the stimulating effects on proliferation of epithelial cells have been already mentioned. The overall effect of the molecule can therefore result in an improvement of the process of tissue repair, with a possible concomitant reduction in the wound healing times. An additional advantage is furthermore connected to the possibility of avoiding the repeated daily medication necessary with the products currently in use.

On the basis of the results obtained and of the brief considerations shown above, the compound, subject of the present invention can be used in all those pathological conditions in which it is necessary to control or eradicate the proliferation in situ of infective pathogenic agents of whichever type, guaranteeing therefore a condition of relative asepticity in the treated tissue, and at the same time promoting the processes of tissue repair. On the basis of the data reported above one can deduce that the product SOS-Ag can be usefully employed in all the pathological conditions of epithelial and cutaneous tissues both intact and lesioned characterised by potential or actual infections sustained by pathogens such as the skin, the mucosa of the oral cavity and internal and external genitals and ocular epithelia. In particular the compound SOS-Ag can be used as a therapeutic agent with disinfectant activity for the prevention and/or treatment of the following pathologies:

infections of the skin both intact and lesioned, of the oral mucosa, of external and internal genitals and of ocular epithelia, brought about by bacteria, fungi, yeasts or viruses (for example candidiasis, acne, herpes, papilloma virus pathologies);

superficial and deep wounds, internal and external, grazes and abrasions, lacerated/contused wounds, wounds with soft tissue loss, strongly exudating wounds both chronic and acute, surgical wounds, traumatic wounds;

superficial and deep burns;

vascular trophic lesions, ischemic ulcers, vascular ulcers, diabetic ulcers, stasis ulcers, corneal ulcers;

bedsores;

athletes foot;

abscesses.

According to the pathology and its severity for the aims of the present invention the compounds can be used in concentrations comprised of between $10^{-5}$ M and $10^{-2}$ M Ag, in topical formulations and in combination with appropriate excipients or diluents compatible with the uses envisaged.

Besides of therapeutic pharmaceutical uses in conditions of clear pathology, the compound can additionally have an useful application in paraphysiological conditions, also with preventive aims, in dermoprotective, lenitive or in cosmetic parapharmaceutical compositions.

These topical formulations can be the more various; the compositions can in fact contain, according to the different applications, the compound of the invention as it is or encapsulated in nanospheres and/or micorspheres based on known or new materials. The compositions can be in form of liquids, semi-solids or solids, containing excipients and/or diluents of pharmaceutical or cosmetic grade (for example solutions and aqueous, non aqueous, hydroalcoholic suspensions, drops, gels, emulsions, creams, ovules, powder sprays, sprays with or without propellants, foams). Furthermore the compound, as it is or encapsulated in nanospheres and/or microspheres constituted by known or new materials, can be supported upon inert biocompatible systems such as films, membranes, patches and dressings, also with a slow release, or can be incorporated into biomaterials, such as for example hydrogels, membranes, sponges, or into materials dissolving rapidly in aqueous environments.

The invention claimed is:

1. Compound of formula (I)

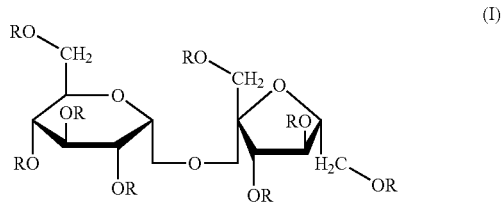

wherein R is $SO_3^-$ $Ag^+$.

2. A topical parapharmaceutical cosmeceutical or cosmetic composition comprising the compound of formula (I)

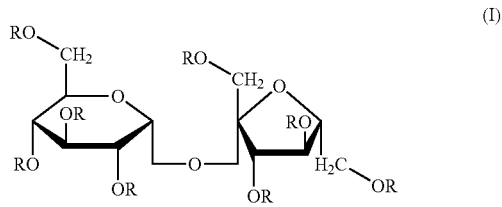

wherein R is $SO_3^-$ $Ag^+$.

3. Compositions comprising, as principal active ingredient, the compound of formula (I)

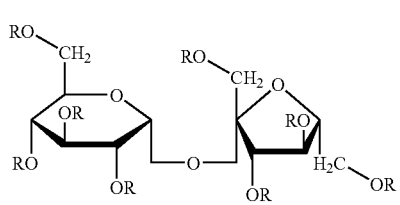

(I)

wherein R is $SO_3^-$ $Ag^+$
in combination with excipients and/or diluents suitable for topical cutaneous, epithelial and mucosal administration.

4. The compositions according to claim 3, in which the compound is combined with excipients and/or diluents suitable for topical cutaneous, epithelial and mucosal administration as it is or encapsulated in nanospheres and/or microspheres.

5. The compositions according to claim 3 in which the compositions are solutions or aqueous, non aqueous, hydroalcoholic suspensiions, drops, gels, emulsions, creams, ointments, ovules, powder sprays, sprays with or without propellants, and foams.

6. The compositions according to claim 3 in which the compound is supported on inert biocompatible systems selected from the group consisting of: films, membranes, patches and dressings, also with slow release.

7. Compositions according to claims 3 or 4 in which the compound is incorporated into biomaterials selected from the group constituted by hydrogels, membranes, sponges, or into materials dissolving rapidly in aqueous environments.

8. A method for prevention and/or cure of infections of bacterial, fungal, viral or yeast origin and in the promotion/acceleration of tissue repair in pathologies of the skin, mucosa and/or oral cavity, and external and internal genitalia and ocular epithelia both intact and lesioned comprising the application of a pharmaceutical composition comprising a compound of formula (I) to the infected area, wherein said compound of formula (I) is:

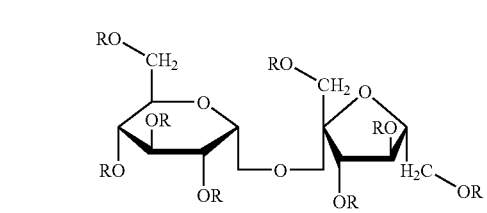

(I)

wherein R is $SO_3^-$ $Ag^+$.

9. The method according to claim 8, wherein the pathologies are selected from the group consisting of: candidiasis, acne, herpes, papilloma virus diseases; superficial and deep wounds, internal and external, grazes and abrasions, lacerated/contused wounds, wounds with soft tissue loss, strongly exudating wounds, both chronic and acute, surgical wounds, traumas; superficial and deep burns; vascular trophic lesions, ischemic ulcers, vascular ulcers, diabetic ulcers, stasis ulcers, corneal ulcers; bedsores; athletes foot; and abscesses.

10. Process for the preparation of compound of formula (I)

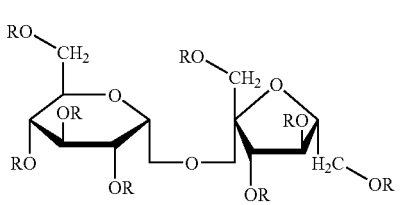

(I)

wherein R is $SO_3^-$ Ag+
characterised by the fact of comprising at least two distinct steps which consist of: a) preparation of sucrose-octosulphate acid starting from a salt of sucrose-octosulphate; b) neutralisation, under controlled conditions up to pH 7,2, of the sucrose-octosulphate acid with Ag ion bases.

11. Process for the preparation of the compound of formula (I)

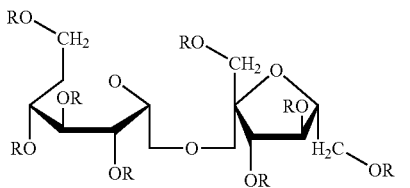

(I)

wherein R is $SO_3^-$ $Ag^+$
characterised by the fact of comprising at least three distinct steps which consist of: a) preparation of sucrose-octosulphate acid starting from a salt of sucrose-octosulphate; b) preparation of a resin derivatised with Ag ions and c) passing the sucrose-octosulphate acid obtained in step a) through the column obtained in step b).

12. Process for the preparation of the compound of formula (I)

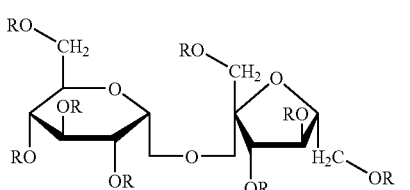

(I)

wherein R is $SO_3^-$ $Ag^+$
characterised by the fact of comprising of a single step of direct exchange between monovalent salts of sucrose-octosulphate and salts of Ag with anions selected from the group constituted by tetrafluoroborate, nitrate, perchlorate and carbonate.

13. The process according to claim 12 in which the anion selected is tetrafluoroborate.

* * * * *